US00PP08291P

United States Patent [19]

Zary

[11] Patent Number: Plant 8,291

[45] Date of Patent: Jul. 6, 1993

[54] ROSE PLANT NAMED JACHAM

[75] Inventor: Keith W. Zary, Thousand Oaks, Calif.

[73] Assignee: Bear Creek Gardens, Inc., Medford, Oreg.

[21] Appl. No.: 796,020

[22] Filed: Nov. 21, 1991

[51] Int. Cl.[5] ..... A01H 5/00

[52] U.S. Cl. ..... Plt./22

[58] Field of Search ..... Plt./14, 16, 22, 23, Plt./25

*Primary Examiner*—Howard J. Locker

*Attorney, Agent, or Firm*—Klarquist, Sparkman, Campbell, Leigh & Whinston

[57] ABSTRACT

A floribunda class rose plant having abundant cut rose production, good vase life of cut blooms, unique flower color, excellent flower petal substance, upright easy-to-manage growth habit, and strong stems.

1 Drawing Sheet

The present invention relates to a new and distinct variety of rose plant of the floribunda class which was originated by me by crossing the variety anKORi, U.S. Plant Pat. No. 5,012, with the variety KORampa, U.S. Plant Pat. No. 5,411.

The primary objective of this breeding was to produce a new rose variety having the productivity and flower color of the male parent KORampa and the larger, stronger stems and greater vase life of the female anKORi. The objective was substantially achieved along with other desirable improvements as evidenced by the following unique combination of characteristics which are outstanding in the new variety and which distinguish it from its parents, as well as from all other varieties of which I am aware:

1. Good production as a greenhouse cut rose variety.
2. Good vase life.
3. Unique flower color.
4. Excellent flower petal substance.
5. Upright easy-to-manage growth habit.
6. Strong stems.

Asexual reproduction of this new variety by budding, as performed at Somis, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color terminology in accordance with the Royal Horticultural Society (London) Colour Chart, except where ordinary dictionary significance of color is indicated.

Parentage:

*Seed parent.*—anKORi, U.S. Plant Pat. No. 5,012.

*Pollen parent.*—KORampa, U.S. Plant Pat. No. 5,411.

Classification:

*Botanical.*—*Rosa hybrida.*

*Commercial.*—Floribunda.

FLOWER

Observations made from specimens grown in a greenhouse environment in Somis, Calif., in February, 1990.

Blooming habit: Continuous.

Bud:

*Size.*—About 1¼ inches long when the petals start to unfurl.

*Form.*—The bud form is long, pointed ovoid.

*Color.*—When sepals first divide, bud color is Orange White Group 159A. When half blown, the upper and lower sides of the petals are Orange White Group 159B.

*Sepals.*—Color: Green Group 138C. Surface texture: There are three normally appendaged sepals. There are two unappendaged sepals with hairy edges.

*Receptacle.*—Color: Green Group 137D. Shape: Funnel. Size: Large. Surface: Smooth.

*Peduncle.*—Length: Medium, averaging about 3 to 3½ inches. Surface: Smooth with occasional small prickles. Color: Medium green. Strength: Stiff, erect.

Bloom:

*Size.*—Medium. Average open diameter is 4 inches.

*Borne.*—Singly and several together, in clusters having pyramidal shape.

*Stems.*—Medium, average length is about 18 to 22 inches.

*Form.*—When first open, bloom has high center. Bloom retains its form to the end, and all petals curl, quill fashion.

*Petalage.*—Number of petals under normal conditions: 30–35.

*Color.*—The upper and reverse sides of the petals are Orange White Group 159B. The base of petals has a small yellowish half-moon at the point of attachment. The major color on the upper side is Orange White Group 159B.

*Variegations.*—Occasional greenish streaks on guard petals.

*Discoloration.*—No discoloration at the end of the first day or even at the end of the third day.

*Fragrance.*—Slight.

Petals:

*Texture.*—Thick, leathery.

*Shape.*—Round.
*Form.*—Tips slightly recurved.
*Arrangement.*—Imbricated, with few petaloids in the center.
*Persistence.*—Petals drop off cleanly before drying.
*Lastingness.*—On the plant: Long, about 5 to 7 days. As a cut flower: Long, about 7 to 8 days.

Reproductive parts:
*Anthers.*—Size: Large. Quantity: Many. Color: Yellow. Arrangement: Regular around styles.
*Filaments.*—Color: White.
*Pollen.*—Color: Gold yellow.
*Styles.*—Color: Red.
*Stigmas.*—Color: Greenish white.

Plant
*Form.*—Bush.
*Growth.*—Vigorous, upright, branching.

Foliage:
*Number of leaflets on normal mid-stem leaves.*—5.
*Size.*—Large, about 6 to 6½ inches long by 5 inches wide.
*Quantity.*—Normal.
*Color.*—New foliage: Reddish. Old foliage: Dark green.

Leaflets:
*Shape.*—Pointed oval.
*Texture.*—Upper side: Smooth.
*Edge.*—Serrated and the young leaf after greening remains edged in red for up to two weeks before completely greening.
*Serration.*—Single, small.
*Petiole rachis.*—Color: Reddish. Petiole edges are lined with small reddish prickles.
*Petiole underside.*—Rough, with prickles.

*Stipules.*—Medium, about ½ inch long, bearded.
*Disease resistance.*—Susceptible to mildew under normal growing conditions at Somis, Calif. As this is a greenhouse rose and not grown outdoors, it has not been tested for rust or blackspot.

Wood:
*New wood.*—Color: Reddish. Bark: Smooth.
*Old wood.*—Color: Green. Bark: Smooth.

Prickles:
*Quantity.*—Few on main canes from base and on laterals from main canes.
*Form.*—Short, about less than 3/16 inch long, straight.
*Color when young.*—Red.

Small prickles:
*Quantity.*—None on main stalks or on laterals.

Other traits, characteristics or markings: Although classed as a floribunda, in cut-flower terms, the variety is an intermediate between floribundas (small flower, short stems—less than 18 inches) and hybrid teas (large flower, long stems—greater than 22 inches). It has 18- to 22-inch stems, a medium-sized flower (4 inches or more when fully open) and produces about 30 stems per plant per year in Somis, Calif.

I claim:

1. A new and distinct variety of rose plant of the floribunda class, substantially as herein shown and described, characterized particularly as to novelty by the unique combination of its flower color, excellent petal substance, long vase life of cut blooms, strong, upright stems, and abundant flower production.

* * * * *

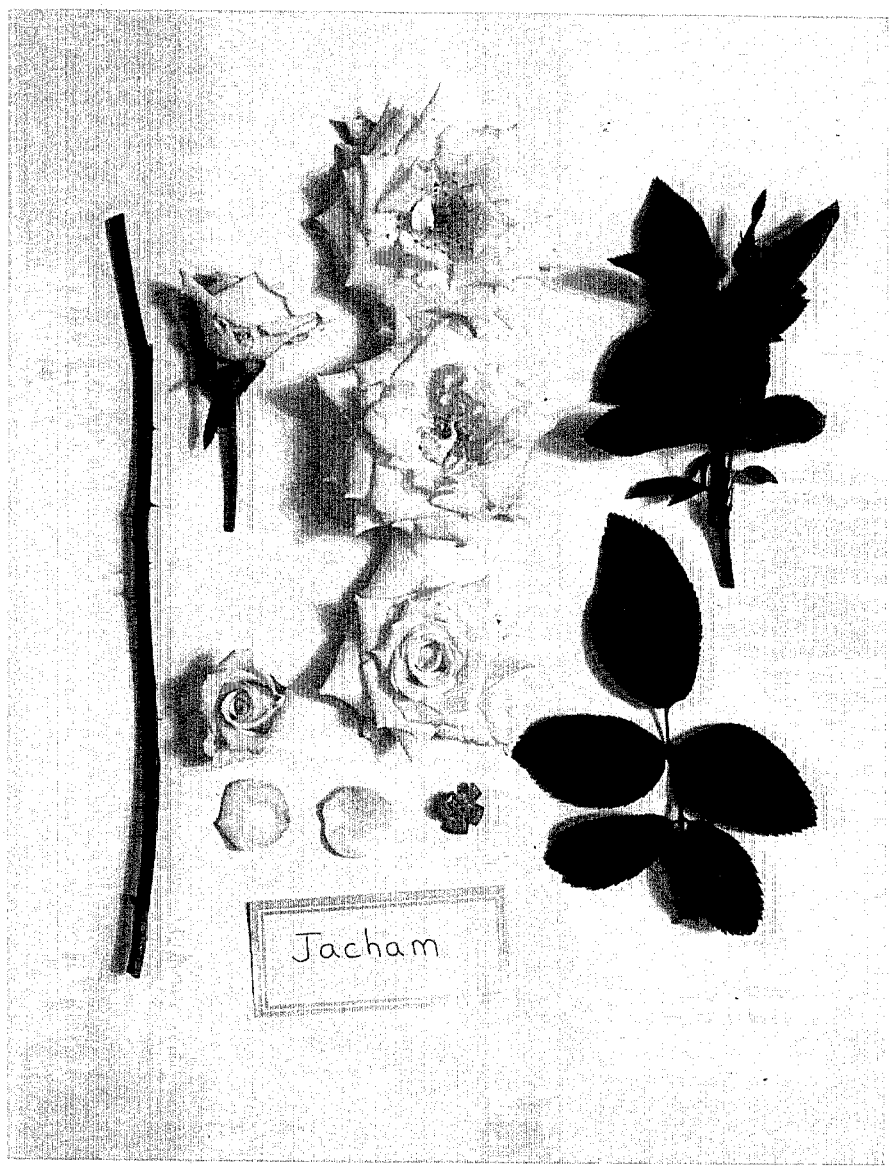
Jacham